US00PP29828P2

(12) United States Plant Patent
Nir

(10) Patent No.: US PP29,828 P2
(45) Date of Patent: Nov. 13, 2018

(54) ***CHAMELAUCIUM* PLANT NAMED 'VEGA'**

(50) Latin Name: *Chamelaucium uncinatum*
Varietal Denomination: VEGA

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 15/731,655

(22) Filed: Jul. 11, 2017

(51) Int. Cl.
*A01H 5/02* (2018.01)

(52) U.S. Cl.
USPC ..... Plt./229

(58) Field of Classification Search
USPC ..... Plt./229
See application file for complete search history.

*Primary Examiner* — Susan McCormick Ewoldt
(74) *Attorney, Agent, or Firm* — Cassandra Bright

(57) ABSTRACT

A new and distinct *Chamelaucium* cultivar named 'VEGA' is disclosed, characterized by abundant bright pink flowers. Flower production begins in Spring. The new variety is a *Chamelaucium*, normally producing cut flower stems, or as a garden or container plant.

2 Drawing Sheets

Figure 1:
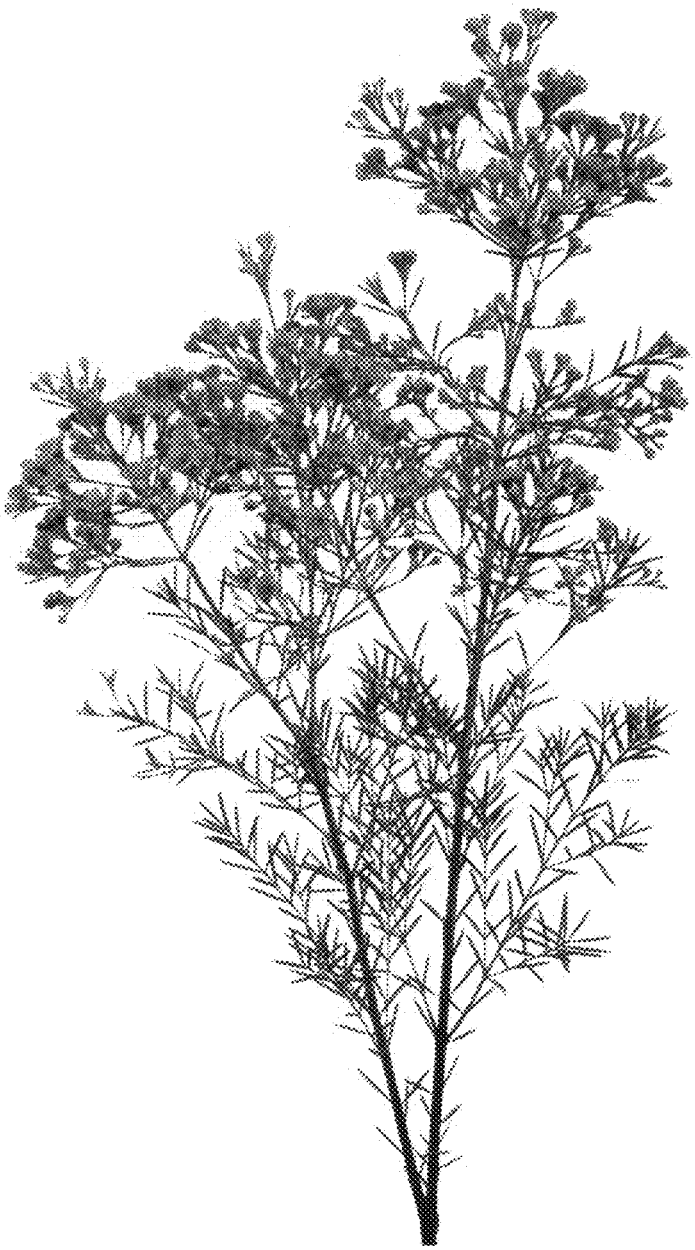

Latin name of the genus and species: *Chamelaucium uncinatum.*

Variety denomination: 'VEGA'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a seedling from the breeding program at a commercial nursery in Kfar Hess, Israel.

The crossing resulting in this new variety was made in March of 2008. The seed parent is the patented variety referred to as *Chamelaucium uncinatum* 'Titan', U.S. Plant Pat. No. 26,181. The pollen parent is the unpatented, proprietary variety referred to as *Chamelaucium uncinatum* 'Z-10'. The new variety was discovered in March of 2011 by the inventor in a group of seedlings resulting from previously mentioned crossing, in a commercial nursery in Kfar Hess, Israel.

Asexual reproduction of the new cultivar has been performed by terminal vegetative cuttings. This was first performed at a commercial nursery in Kfar Hess, Israel in May of 2011 and has shown that the unique features of this cultivar are stable and reproduced true to type in at least 4 successive generations.

SUMMARY OF THE INVENTION

The cultivar 'VEGA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VEGA'.

These characteristics in combination distinguish 'VEGA' as a new and distinct *Chamelaucium* cultivar:

1. Blooming season begins in Spring, in Kfar Hess, Israel.
2. Bright pink flowers with a dark eye.
3. Abundant flowering.

PARENT COMPARISON

Plants of the new cultivar 'VEGA' are similar to plants of the seed parent in most horticultural characteristics, however, plants of the new cultivar 'VEGA' differ in the following:

1. Flower color of the new variety is much brighter pink than 'Titan', with a different colored eye.
2. The new variety begins flowering in Spring, 'Titan' begins flowering in the Winter months.

Plants of the new cultivar 'VEGA' are similar to plants of the pollen parent in most horticultural characteristics, however, plants of the new cultivar 'VEGA' differ in the following:

1. The new variety is begins flowering in Spring, the pollen parent blooms from January until March.
2. Flower size of the new variety is larger.
3. The new variety produces flowers and buds more abundantly.

COMMERCIAL COMPARISON

Plants of the new cultivar 'VEGA' are comparable to the variety *Chamelaucium uncinatum* 'Mars', U.S. Plant Pat. No. 26,275. The two *Chamelaucium* varieties are similar in most horticultural characteristics; however, the new variety 'VEGA' differs in the following:

1. The new variety begins flowering in the Spring, this comparator variety begins flowering from December through February.
2. Eye color of the new variety is darker.

Plants of the new cultivar 'VEGA' can also be compared to the commercial variety *Chamelaucium uncinatum* 'Rotem Wax', U.S. Plant Pat. No. 26,024. These varieties are similar in most horticultural characteristics however, the new variety 'VEGA' differs in the following:

1. The new variety begins flowering in the Spring, this comparator variety begins flowering from December through February.
2. The new variety produces more flowers and buds per stem than this comparator.

BRIEF DESCRIPTION OF THE PHOTOGRAPHS

The accompanying photograph in FIG. 1 illustrates in full color a close up of typical flowers and foliage of 'VEGA' on a mature stem at approximately 1 year of age.

Figure 2:
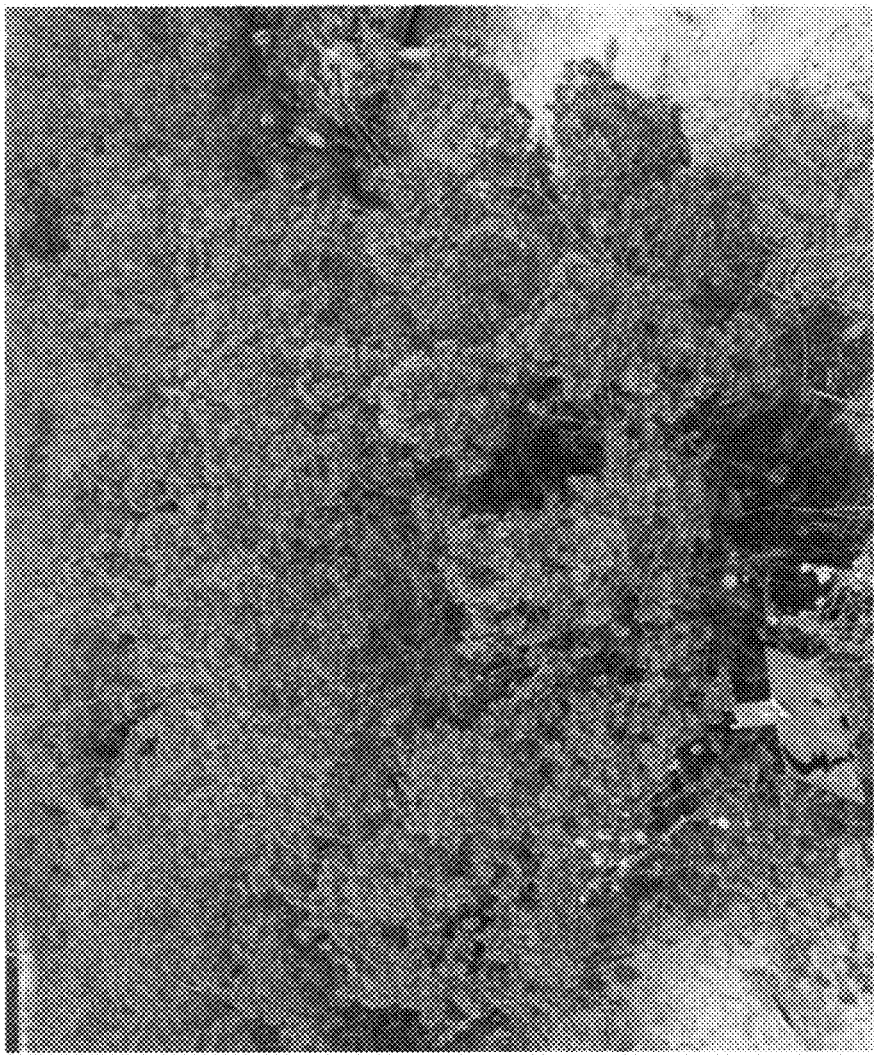

FIG. 2 illustrates a plant of the new variety at approximately 1 to 2 years of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'VEGA' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'VEGA'.

Age of plant described: About 2 months old from a rooted cutting.

Typical flowering stems harvested per plant: About 100 during the course of the season.

Vase life of flowers: Two weeks.

PROPAGATION

Time to produce a rooted plantlet: 30 to 60 days at approximately 24° C.

Root description: Semi-woody to fibrous. Greyed-Brown in color, not accurately measured with R.H.S. chart.

PLANT

Growth habit: Upright plant produces multiple stems from a pinch, or after harvesting stems.

Height: 200 cm.

Plant spread: 80 cm.

Growth rate: Rapid.

Branching characteristics: Moderate to high branching occurs after pinching.

Length of primary lateral branches: 60 cm to 90 cm on average.

Diameter of lateral branches: 0.15 cm.

Quantity of primary lateral branches: 100, these are the harvested flowering stems.

Characteristics of primary lateral branches:

*Form*.—Round.

*Diameter*.—0.45 cm, measured at 50 cm from top.

*Color*.—Near RHS Grey-Green 197A, lower branch near Brown 200C with an overlay of Greyed-Green N189A.

*Texture*.—Smooth.

*Strength*.—Stems somewhat brittle.

Internode length: Range from 2.0 to 6.5 cm.

FOLIAGE

Leaf:

*Arrangement*.—Opposite.

*Quantity*.—Approximately 4 leaves, in the 5-10 cm section from the top of the branch.

*Average length*.—1.6 cm.

*Average width*.—0.1 cm.

*Shape of blade*.—Needle.

*Apex*.—Acute.

*Base*.—Attenuate.

*Margin*.—Entire.

*Texture*.—Glabrous all surfaces.

*Pubescence*.—None.

*Aspect*.—Straight, occurring at approximately a 30 to 45 degree angle.

*Color*.—Young foliage: Near RHS Green 137C. Mature foliage: Near RHS Green 137A.

*Venation*.—Indistinguishable from foliage.

*Petiole*.—Not present.

FLOWER

Natural flowering season: Flowering begins in Spring, without a juvenility period in Kfar Hess, Israel. Plants flower continuously under short day conditions.

Days to flowering from rooted cutting: Approximately 45 to 70 days.

Inflorescence type: Terminal Panicle.

Individual flower type: Single, rotate 5 petaled with a cone shaped hypanthium. Flowers outwardly and upwardly facing.

Persistent or self-cleaning: Self-Cleaning.

Lastingness: About 2 weeks in a vase. Approximately 45 to 70 days on the plant.

Typical flowering stem length: Approximately 60 to 80 cm.

Bud:

*Shape*.—Slightly flattened sphere.

*Length*.—0.4 cm.

*Diameter*.—0.5 cm.

*Color*.—Near RHS Red 53D.

Inflorescence size:

*Diameter*.—Average 10 to 15 cm.

*Length*.—Average 15 to 25 cm.

Flower size:

*Diameter*.—Average 1.6 cm.

*Length*.—Average 0.9 cm.

Corolla:

*Petals*.—Arrangement: Rotate, not overlapping. Length: Average 0.6 cm. Diameter: Average 0.6 cm. Quantity: 5. Attitude: Semi-Erect. Texture: Smooth. Apex: Obtuse rounded. Base: Fused into a hypanthium.

*Color*.—When opening: Upper surface: Near RHS Red-Purple 72B. Lower surface: Near RHS Red-Purple 72B. Fully opened: Upper surface: Near RHS Red-Purple 72B. Lower surface: Near RHS Red-Purple 72B. Aging: Upper surface: Near RHS Red-Purple 72B. Lower surface: Near RHS Red-Purple 72B.

Hypanthium:

*Diameter.*—0.7 cm.

*Length.*—0.3 cm.

*Color.*—When opening: Upper surface: Near RHS Yellow-Green 146C. Lower surface: Near RHS Yellow-Green 146C. Fully opened: Upper surface: Near RHS Greyed-Purple 183A. Lower surface: Near RHS Greyed-Purple 183A. Aging: Upper surface: Near RHS Greyed-Orange 166A. Lower surface: Near RHS Greyed-Orange 166A.

*Diameter.*—Average 0.3 cm.

*Length.*—Average 0.7 cm.

*Shape.*—Obconical.

Calyx/sepals:

*Quantity per flower.*—Fused into a single, conical structure.

*Length.*—0.3 cm.

*Width.*—0.7 cm.

*Margin.*—Entire.

*Texture.*—Smooth.

*Color.*—When opening: Inner surface: Near RHS Yellow-Green 146C. Outer surface: Near RHS Yellow-Green 146C. Fully opened: Inner surface: Near RHS Yellow-Green 146C. Outer surface: Near RHS Yellow-Green 146C. Aging: Inner surface: Near RHS Yellow-Green 146C. Outer surface: Near RHS Yellow-Green 146C.

Peduncle: Peduncle consists of the plant stem.

Pedicel:

*Length.*—1.0 cm.

*Diameter.*—0.1 cm.

*Color.*—Near RHS Yellow-Green 146C.

Fragrance: None.

REPRODUCTIVE ORGANS

Stamens:

*Number.*—10.

*Filament length.*—1.5 mm.

*Filament color.*—Near RHS Yellow-Green 154D.

Anthers:

*Shape.*—Oval.

*Length.*—0.5 mm.

*Width.*—0.2 mm.

*Color.*—Near RHS Grey-Brown 199A.

Pollen: Not observed.

Pistil:

*Number.*—1.

*Style length.*—0.5 cm.

*Style color.*—Near RHS White 155B.

*Stigma.*—Shape: Round. Color: Near RHS Purple N77B. Texture: Glabrous.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1 mm, brown in color, too minute to accurately measure color with R.H.S. chart.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named 'VEGA' as herein illustrated and described.

* * * * *